(12) United States Patent
Meckel et al.

(10) Patent No.: US 11,622,885 B2
(45) Date of Patent: Apr. 11, 2023

(54) ILLUMINATED VITRECTOMY CUTTER WITH ADJUSTABLE ILLUMINATION APERTURE

(71) Applicant: Alcon Research, LLC, Fort Worth, TX (US)

(72) Inventors: Jon-Peter Meckel, Phoenix, AZ (US); Matthew Edward Bazydlo, Costa Mesa, CA (US); Christopher McCollam, Irvine, CA (US)

(73) Assignee: Alcon Inc., Fribourg (CH)

( * ) Notice: Subject to any disclaimer, the term of this patent is extended or adjusted under 35 U.S.C. 154(b) by 845 days.

(21) Appl. No.: 16/416,743

(22) Filed: May 20, 2019

(65) Prior Publication Data

US 2019/0269556 A1    Sep. 5, 2019

Related U.S. Application Data

(63) Continuation of application No. 14/064,326, filed on Oct. 28, 2013, now abandoned.

(60) Provisional application No. 61/721,216, filed on Nov. 1, 2012.

(51) Int. Cl.
    *A61F 9/007*    (2006.01)
    *A61F 9/008*    (2006.01)

(52) U.S. Cl.
    CPC ...... *A61F 9/00736* (2013.01); *A61F 9/00821* (2013.01); *A61F 2009/00863* (2013.01); *A61F 2009/00874* (2013.01)

(58) Field of Classification Search
    CPC .......................... A61F 9/00736; A61F 9/00821

USPC ........................................................ 600/249
See application file for complete search history.

(56) References Cited

U.S. PATENT DOCUMENTS

| | | | |
|---|---|---|---|
| 5,413,574 A | 5/1995 | Fugo | |
| 5,611,799 A | 3/1997 | Smith | |
| 6,382,968 B2 | 5/2002 | Livaditis | |
| 6,480,279 B2 | 11/2002 | Nara et al. | |
| 7,182,763 B2* | 2/2007 | Nardella | A61B 17/068 606/49 |
| 7,881,573 B2* | 2/2011 | Eberle | A61B 1/0017 385/115 |
| 8,485,972 B2 | 7/2013 | Papac et al. | |
| 9,072,587 B2 | 7/2015 | Smith | |
| 10,307,290 B2 | 6/2019 | Kern | |
| 10,376,414 B2 | 8/2019 | Hallen | |
| 10,478,266 B2 | 11/2019 | Mirsepassi | |
| 2006/0184162 A1 | 8/2006 | Smith | |
| 2007/0255264 A1* | 11/2007 | Hickingbotham | A61F 9/007 606/2 |
| 2008/0004608 A1* | 1/2008 | Dacquay | A61F 9/00821 606/4 |
| 2008/0177257 A1 | 7/2008 | Smith et al. | |

(Continued)

*Primary Examiner* — Si Ming Ku

(57) ABSTRACT

A vitrector that includes an adjustable illumination aperture is described. The vitrector may include a probe and a light sleeve assembly extending along and substantially surrounding the probe. The light sleeve assembly may include a plurality of optical fibers. At least a portion of the optical fibers are operable to provide illumination so as to define an illumination aperture about the vitrectomy probe. A portion of the optical fibers may be encapsulated. The light sleeve assembly may be adjustable along a length of the probe, providing adjustment of the illumination aperture to increase or decrease an area of illumination provided thereby.

19 Claims, 7 Drawing Sheets

(56) References Cited

U.S. PATENT DOCUMENTS

| | | | |
|---|---|---|---|
| 2009/0182313 A1* | 7/2009 | Auld | A61B 17/28 606/15 |
| 2009/0253967 A1* | 10/2009 | Gill | A61B 1/00142 600/249 |
| 2011/0125139 A1 | 5/2011 | Auld | |
| 2012/0035425 A1* | 2/2012 | Schaller | B29C 45/14622 600/249 |
| 2013/0012783 A1* | 1/2013 | Vayser | A61B 1/07 600/249 |
| 2014/0163542 A1 | 6/2014 | Vezzu | |
| 2019/0282322 A1 | 9/2019 | Mirsepassi | |
| 2020/0022773 A1 | 1/2020 | Grueebler | |

* cited by examiner

ILLUMINATED VITRECTOMY CUTTER WITH ADJUSTABLE ILLUMINATION APERTURE

CROSS REFERENCE TO RELATED APPLICATIONS

This application is a continuation of U.S. Non-Provisional application Ser. No. 14/064,326, filed Oct. 28, 2013, which is entitled "Illuminated Vitrectomy Cutter With Adjustable Illumination Aperture" and claims priority to U.S. Provisional Application No. 61/721,216 filed Nov. 1, 2012, which is entitled "Illuminated Vitrectomy Cutter With Adjustable Illumination Aperture", both of which are hereby incorporated by reference in their entirety as though fully and completely set forth herein.

TECHNICAL FIELD

The present disclosure relates generally to the field of vitrectomy cutters, and more particularly, to illuminated vitrectomy cutters with adjustable illumination apertures for providing adjustment of an area of illumination provided about the cutter tip.

BACKGROUND

Vitrectomy cutters generally are used during ophthalmic surgeries such as vitreo-retinal surgeries that involve the surgical removal of the vitreous in the eye. The vitreous includes a clear, colorless, gel-like substance that fills the eye from the iris to the retina. During some surgeries to correct impaired vision, a vitrectomy cutter generally can be used to cut and remove portions of the vitreous as needed to correct the visual impairment.

Vitrectomy cutters can include a hollow, reciprocating probe having an opening or port at the cutting end of the probe, and can be connected to a vacuum for drawing fluid and tissue away from the surgical site. During a vitreo-retinal surgery, the internal portions of the eye where the incision/correction is being performed may require illumination, especially where the incision is of a reduced or minimal size to enable the surgeon to clearly see and accurately remove portions of the vitreous in order to correct the visual impairment. In the past, separate illumination probes have been used to provide focused illumination of the eye at the surgical site. Additionally, some vitrectomy cutters with illumination capability have been developed. However, these existing vitrectomy cutters provide fixed illumination, while in use a surgeon may need to vary or otherwise change or adapt the area of illumination during the surgical procedure.

Accordingly, there is a need for an illuminated vitrectomy instrument that is capable of providing adjustment of an illumination aperture to increase or decrease an area of illumination provided thereby.

SUMMARY

According to one aspect, the present disclosure generally relates to an illuminated vitrectomy instrument that may include a probe and a light sleeve assembly. The light sleeve assembly may extend along and substantially surrounding the probe and have a position adjustable along a length of the probe. The light sleeve assembly may include a plurality of optical fibers. At least a portion of the optical fibers may be operable to provide illumination. Also, each of the optical fibers includes an end face. The light sleeve assembly may also include an illumination aperture. The illumination aperture is defined by end faces of the optical fibers and is operable to provide an area of illumination. The area of illumination may be varied in response to the position of the light sleeve assembly relative to the probe.

Another aspect of the disclosure encompasses an illuminated vitrectomy cutter assembly including a housing, a probe having a proximal end received within the housing and a freely extending distal end, and a light sleeve assembly. The light sleeve assembly may be movable along the probe between the proximal end and distal end of the probe. The light sleeve assembly also includes a first end adjacent to the housing; a second end opposite the first end; and a plurality of optical fibers arranged in an array about the probe. At least a portion of the plurality of optical fibers may be operable to provide illumination. Also, each of the optical fibers includes an end face. The light sleeve assembly may also include an illumination aperture formed at the second end thereof. The illumination aperture is defined by the end faces of the optical fibers, and the illumination aperture is operable to provide collective illumination of the plurality of optical fibers. The collective illumination includes the individual illumination from each of the plurality of optical fibers.

The various aspects may include one or more of the following features. A nose piece may be included that at least partially houses the probe. A proximal end of the light sleeve assembly may be received within the nose piece, and a distal end of the light sleeve assembly may terminate proximally to a distal end of the probe. A distance between the distal end of the light sleeve assembly and the distal end of the probe may be altered in response to a change in the position of the light sleeve assembly relative to the probe. The position of the light sleeve assembly may be manually adjustable. An actuator may be coupled to the light sleeve assembly. The position of the light sleeve assembly with respect to the probe may be adjusted by manipulation of the actuator.

The light sleeve assembly may further include a sleeve. The plurality of optical fibers may be arranged in an array along an inner surface of the sleeve. The light sleeve assembly may also include an encapsulant encapsulating the plurality of optical fibers. The sleeve may be adapted to be connected to a first pole of a generator. The probe may be adapted to be connected to a second pole of the generator. The encapsulant may define an insulating layer disposed between the sleeve and the probe. An alternating current applied to the sleeve and the probe may be operable to generate an electric field therebetween to produce a diathermy function when the distal end of the light sleeve assembly is positioned substantially flush with the end surface of the probe. At least one of plurality of optical fibers may be a fiber operable to propagate laser light.

The various aspects may also include one or more of the following features. The collective illumination of the plurality of optical fibers may define an area of illumination, and the area of illumination may be adjusted in response to movement of the light sleeve assembly along the probe. A nose piece may be coupled to the housing. The nose piece may be adapted to receive a proximal end of the light sleeve assembly. The light sleeve assembly may also include a sleeve. The plurality of optical fibers may be arranged in an array along an inner surface of the sleeve. The light sleeve assembly may also include an encapsulant substantially encapsulating the plurality of optical fibers along at least a portion of the sleeve. The sleeve may be adapted to be connected to a first pole of a generator. The probe may be adapted to be connected to a second pole of a generator. The encapsulant may define an insulating layer disposed between the sleeve and the probe. Upon application of an alternating current to the sleeve and the probe, an electric field is generated between the sleeve and the probe to produce a diathermy function when the second end of the light sleeve assembly is positioned substantially flush with an end surface of the probe. At least one of the plurality of optical fibers may be a fiber capable operable to propagate laser light.

The details of one or more implementations of the present disclosure are set forth in the accompanying drawings and the description below. Other features, objects, and advantages will be apparent from the description and drawings, and from the claims.

Those skilled in the art will appreciate and understand that, according to common practice, the various features of the drawings discussed below are not necessarily drawn to scale, and that dimensions of various features and elements of the drawings may be expanded or reduced to more clearly illustrate the example implementations of the present disclosure.

DETAILED DESCRIPTION

The drawings illustrate various example implementations of a vitrectomy instrument (interchangeably referred to as "vitrector") having illumination capability that provides the ability of selectively adjusting an area of illumination provided about a distal end or cutting tip of the vitrector.

Figure 1A:
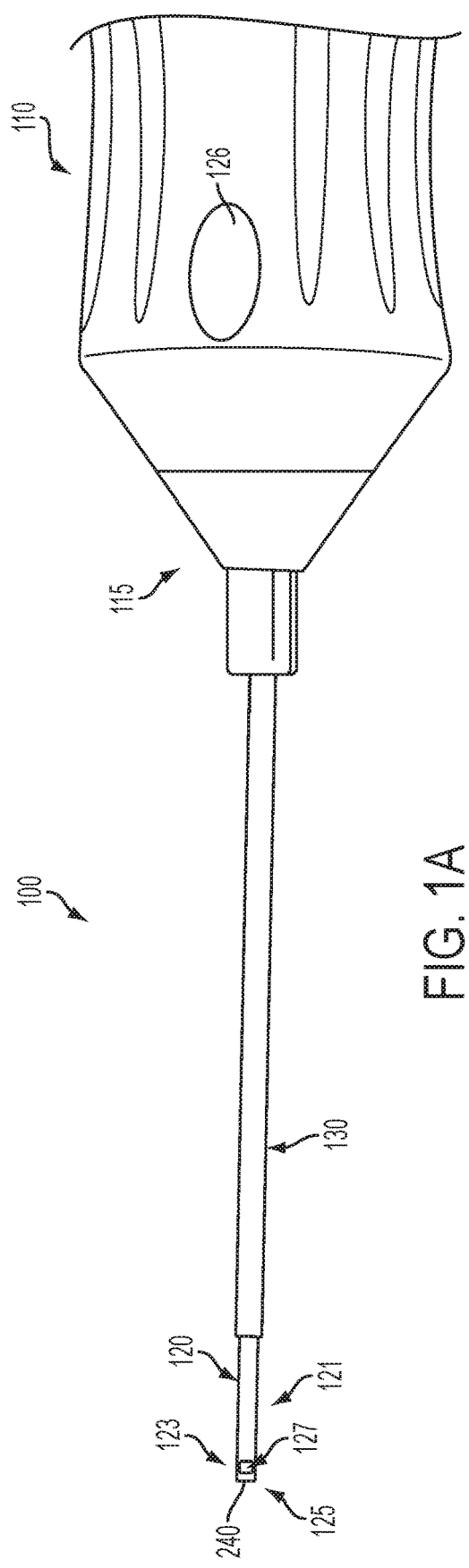
FIG. 1A is a side view of an example illuminated vitrectomy cutter assembly.
Figure 1B:
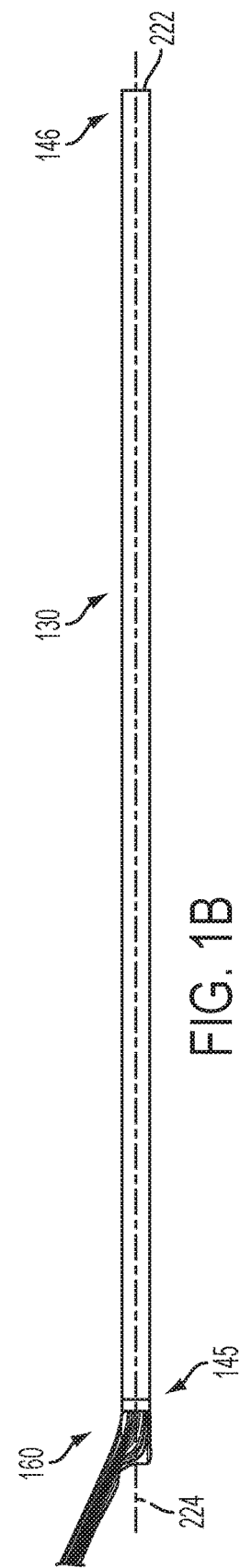
FIG. 1B is a side view of an example light sleeve assembly.
Figure 1C:
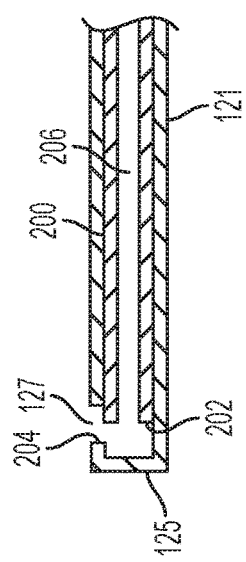
FIG. 1C is a partial cross-sectional view of a distal end of an example vitrectomy cutter probe.

FIGS. 1A through 1B illustrate and example vitrector 100. The vitrector 100 may include a housing 110 having a nose piece 115 extending therefrom. The vitrector 100 may also include a hollow vitrectomy probe or needle (referred to hereinafter as "probe") 120 having an outer cutting member 121. A proximal end of the outer cutting member 121 may be received within or otherwise coupled to housing 110. A distal end 123 of the outer cutting member 121 includes a cutting tip 125. As shown in FIG. 1C, in some implementations, the probe 120 may also include an inner cutting member slideable within the outer cutting member 121. The inner cutting member 200 may have a cutting edge 202. As material is drawn into a port 127 formed in the outer cutting member 121, the edge 202 of the inner cutting member 200 along with an edge 204 defining the port 127 cooperate to sever material (e.g., tissue) drawn into the port 127 as the inner cutting member 200 is reciprocated within the outer cutting member 121. The severed material along with other fluids and material drawn through the port 127 may be aspirated away through a lumen 206 defined by the inner cutting member 200.

The housing 110 may house at least a portion of a drive mechanism. The drive mechanism is operable to reciprocate the inner cutting member 200 within and relative to the outer cutting member 121. The housing 110 may also provide one or more ports. For example, the one or more ports may provide a connection between the vitrector 100 and a vacuum source for aspiration. In some implementations, another port may be used to provide pressurized air, for example, to operate the drive mechanism. In other implementations, a port may provide electrical power for the drive mechanism. The housing 110 may also include a tactile indicator 126. The tactile indicator 126 may provides a tactile indication to a user, such as a surgeon or other medical professional, regarding a side on which of the outer cutting member 121 the port 127 is located.

The nose piece 115 extends from the housing 110 and couples the probe 120 to the housing 110. In some instances, a length of the probe 120 may be approximately 15 mm to 27 mm. However, in other implementations, the probe may have a larger or smaller length. Various outer diameter vitrectomy probes may also be used. For example, in some instances, the probes may be 20 gauge, 23 gauge, 25 gauge, or 27 gauge. In other instances, the probe may have any a size larger or smaller than those indicated.

Referring to FIGS. 1A and 1B, the vitrector 100 may also include a light sleeve assembly 130. The light sleeve assembly 130 includes a proximal end 145 adjacent the housing 110 and a distal end 146 spaced from the proximal end. The light sleeve assembly 130 may be received onto and substantially surrounds the probe 120. The distal end 146 of the light sleeve assembly 130 is disposed proximate the distal end 123 of the probe 120. Additionally, the proximal end 145 of the light sleeve assembly 130 may be slidably received within the nose piece 115. Thus, the light sleeve assembly 130 is configured to be slideable on and relative to the probe 120.

Figure 2:
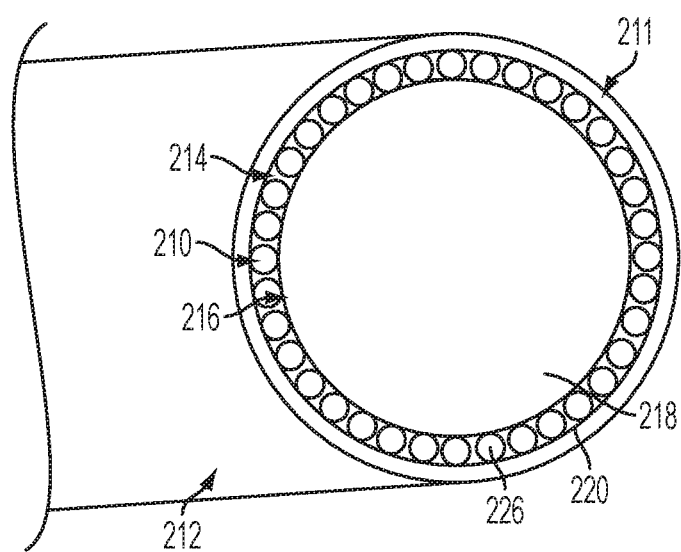
FIG. 2 is a perspective view of a distal end of an example light sleeve assembly.

FIG. 2 illustrates a cross-section view of the distal end 146 of an example light sleeve assembly 130. The light sleeve assembly 130 defines a central bore 218 into which the probe 120 is received. The light sleeve assembly 130 may include a plurality of optical fibers 210 arranged in a substantially circular array about the light sleeve assembly 130. The distal end surfaces 226 of the plurality of optical fibers 210 define an illumination aperture 220. Light sleeve assembly 130 may also include an outer sleeve 212. In some implementations, the outer sleeve 212 may be formed from a rigid material. For example, in some instances, the outer sleeve 212 may be formed from a metal, a polymer, or any other suitable material. The optical fibers 210 may be arranged in a circular array along an inner surface of the sleeve 212. In some implementations, the light sleeve assembly 130 may include other types of fibers. For example, in some implementations, the light sleeve assembly 130 may include one or more fibers operable to transmit other types of radiation. For example, fibers that transmit laser light, ultraviolet light, infrared light, or any other type of light may also be included. Further, in some implementations, the light sleeve assembly 130 may also include one or more spacers disposed between fibers. The spacers are operable to separate adjacent fibers a desired amount.

The optical fibers 210 extend substantially along the length of the probe 120, with proximal ends of some or all of the optical fibers generally being received within the housing 110. One or more of the optical fibers 210 may be coupled to an illumination source. Example illumination sources may include an ultraviolet ("UV") source, an infrared ("IR") source, or other desired light or radiation source. While "light" is discussed herein, the scope of the disclosure is not intended to be limited to visible light. On the contrary and as indicated above, other types of radiation, such as UV and IR radiation, may be transmitted through and emitted from one or more of the optical fibers 210. The term "light" is intended to encompass any type of radiation for use with the optical fibers 210. Further, in some instances, the optical fibers 210 may be multi-mode end-emitting fibers. However, in other implementations, other types of light-emitting optical fibers may be used.

Light from an illumination source may be conveyed through one or more of the optical fibers 210 and emitted from distal ends 211 thereof. As explained above, the end surfaces 226 of the optical fibers at distal ends 211 thereof collectively define the illumination aperture 220. In some implementations, the optical fibers may have a diameter in the range of 25 μm to 75 μm. In some particular implementations, the optical fibers 210 may have a diameter within the range of about 40 μm to 50 μm. In still other implementations, one or more of the optical fibers 210 may have a diameter that is larger or smaller than the diameters described. In some implementations, the light sleeve assembly 130 may have a plurality of optical fibers 210 that are all the same size. In other implementations, the light sleeve assembly 130 may have optical fibers 210 of varying sizes.

Additionally, the light sleeve assembly 130 may include an encapsulant 214 that substantially encapsulates the optical fibers 210 along at least a portion of the length of the sleeve 212. The encapsulant 214 may be formed of a polymer, such as a resin. In other instances, the encapsulant 214 may include other material, such as a rubber, a tape, or any other desired encapsulant or sealing materials, or any combination of two or more of these materials.

In some instances, the sleeve 212, optical fibers 210, and encapsulant 214 may be polished together to form an end face 222 at the distal end 146 of the light sleeve assembly 130. In some implementations, the end face 222 may be planar, as shown in the example light sleeve assembly 130 of FIG. 1B. In some instances, the end face 222 may be perpendicular to the longitudinal axis 224 of the light sleeve assembly 130 as also illustrated in FIG. 1B. In other instances, the end face 22 may be formed at an angle relative to the longitudinal axis 224. In other instances, the end face 222 may not be planar. Rather, in some instances, the distal end 146 may have an end face that has an irregular profile. For example, the end face 222 may be wavy or be faceted, or have any other desired shape or profile. In some instances, the sleeve 212, optical fibers 210, and encapsulant 214 extend along substantially the entire length of the light sleeve assembly 130, with an inner surface 216 of the encapsulant 214 defining the bore 218 that is configured to receive the probe 120.

Referring again FIGS. 2 3B, 3C, and 4B, each of the optical fibers 210 includes an end surface 226. Also, at least a portion of the optical fibers 210 are operable to provide illumination via the end surfaces 226. As explained above, the end surfaces 226 providing illumination collectively define the illumination aperture 220. As also explained above, the light sleeve assembly 130 includes an end face 222. Thus, the illumination aperture 220 may be defined within the end face 222.

The illumination aperture 220 may be defined in any desired configuration. For example, in some implementations, the illumination aperture 220 may have a semicircular shape. In other implementations, the illumination aperture 220 may have a continuous circular shape. In still others, the illumination aperture 220 may have an arc length of any desired length. Further, one or more optical fibers 210 providing illumination may be separated from one or more additional optical fibers 210 also providing illumination by one or more spacers. Thus, the illumination aperture 220 may be configured into any desired area or pattern about the probe 120. Further, the cross-sectional shape of the light sleeve assembly 130 is not limited to a circular shape. Rather, the light sleeve assembly 130 may have any shape and, particularly, may have a shape associated with the shape of the probe 120 to which the light sleeve assembly 130 is coupled.

Figure 3A:
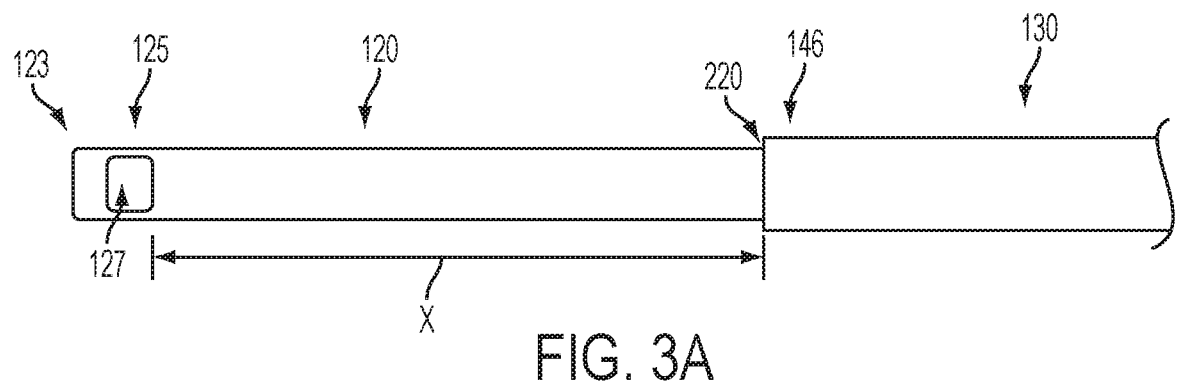
FIG. 3A is detailed view of a distal end of an example vitrectomy cutter probe.
Figure 3B:
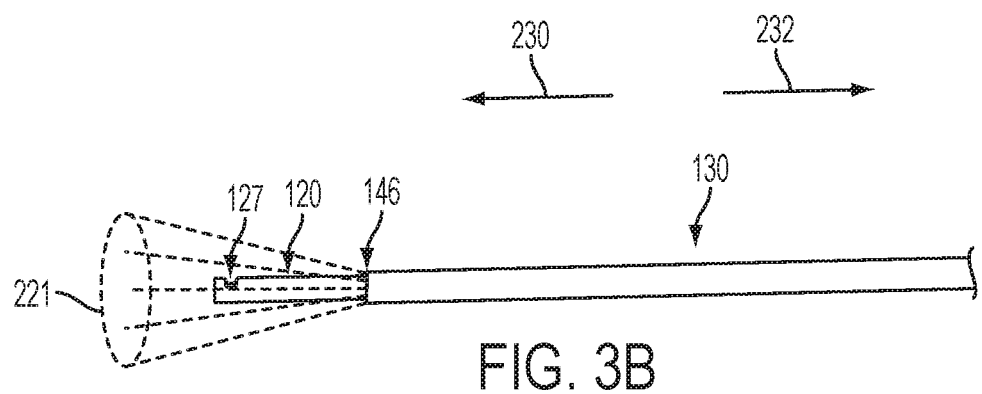
FIGS. 3B and 3C are side views of the distal end of the vitrectomy cutter probe with the light sleeve assembly disposed at different positions relative to the vitrectomy cutter probe.
Figure 3C:
Figure 4B:
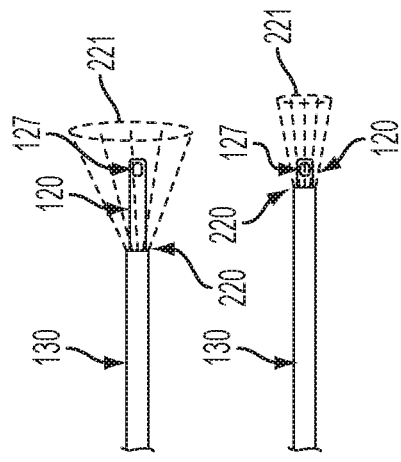
FIGS. 4A to 4B are side views depicting a movement of the light sleeve assembly with respect to the distal end of the vitrectomy cutter probe.

Referring to FIGS. 3A, 3B, and 3C, the light sleeve assembly 130 may be movable along the probe 120. As the light sleeve assembly 130 is extended (i.e., moved in a direction of arrow 230) or retracted (i.e., moved in a direction of arrow 232) along the probe 120, a position of the illumination aperture 220 is adjusted with respect to the cutting tip 125 of probe 120. Movement of the light sleeve assembly 130 relative to the probe 120 adjusts a size of an illumination area 221 provided by the illumination aperture 220, as shown in FIGS. 3B, 3C, and 4B. For example, a user may desire that an area of a retina be illuminated. Thus, the illumination area 221 may be a portion of the retina for which illumination is desired. A user may adjust the size of the illumination area 221 by sliding the light sleeve assembly 130 relative to the probe 120. The lux (i.e., luminous flux per unit area) of the illumination from the illumination aperture 220 may also be altered based on the position of the light sleeve assembly 130 relative to the probe 120. Thus, the illumination aperture 220 may be adjusted with respect to the cutting tip 125 of the probe 120 to vary the illumination provided about the cutting tip 125 through the illumination aperture 220.

As depicted in FIG. 3A, a region "x" defines a distance between the distal end 146 of the light sleeve assembly 130 and the distal end 123 of the probe 120 and, particularly, the cutting tip 125. The light sleeve assembly 130 may be adjusted to any position within this distance "x" to cause alteration of the size of the illumination area 221, as shown in FIGS. 3B and 3C. Light sleeve assembly 130 is adjustable along a length of the vitrectomy needle 120 to provide adjustment of the illumination aperture 220 to increase or decrease the area of illumination 221 provided thereby. During the course of a surgical procedure, such as a vitreoretinal surgical procedure, a surgeon may desire different levels of illumination at any given time. For example, a surgeon may desire different levels of illumination in different regions of the eye, or a surgeon may desire adjusting an amount of illumination in any particular region of the eye. By adjusting the illumination area 121 by varying the position of the illumination aperture 220 within the region "x" relative to the port 127, the illumination provided via the illumination aperture 220 may be tailored to specific needs of a user, such as a surgeon performing the surgical procedure.

Figure 4A:
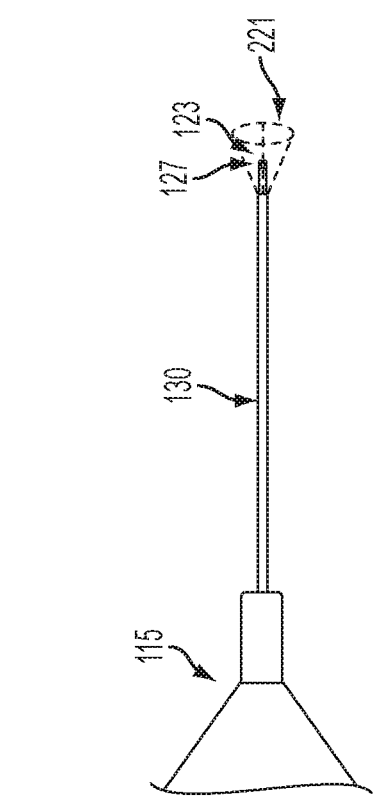

Referring to FIGS. 4A-4B, in some implementations, the light sleeve assembly 130 (and, consequently, the illumination aperture 220) may be moved along the probe 120 by manually sliding the light sleeve assembly 130 to one or more positions along the probe 120. The light sleeve assembly 130 may be adjusted to any desired position along the probe 120 within a range of positions. This allows a user to position the illumination aperture 220 at desired positions along the probe 120 and with respect to the cutting tip 125 thereof. As a result, an amount of illumination provided via the illumination aperture 220 and directed to an illumination area 221 may be varied. For example, in some instances where a focused light (or smaller, more directed area of illumination) is desirable, the light sleeve assembly 130 may be moved closer to the distal end 123 of the probe 120. For example, in some implementations, the light sleeve assembly 130 may be moved to within 1 to 15 mm or closer of the cutting tip 125. In some implementations, the distal end 146 of the light sleeve assembly 130 may be extended to a position that is substantially flush with or partially extending past an end surface of the cutting tip 125. In other cases where a diffused illumination or an enlarged area of illumination is desirable (for peripheral viewing, for example), the light sleeve assembly 130 may be moved farther away from the distal end 123 of the probe 120 so as to allow greater spreading of the illumination from the illumination aperture 220.

Figure 5B:
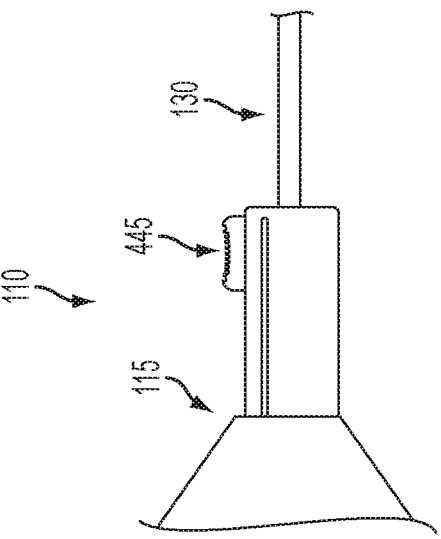
FIGS. 5A to 5B illustrate an example actuator adapted operable to extend or retract the light sleeve assembly relative to the vitrectomy cutter probe at different positions.
Figure 5A:
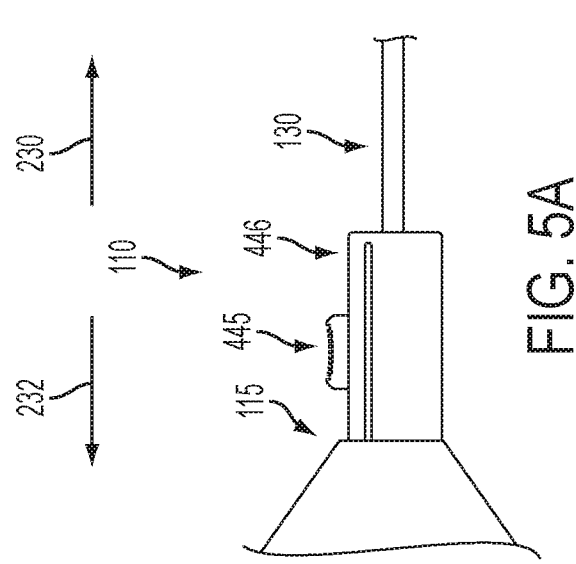

In some implementations, the light sleeve assembly 130 and, correspondingly, the illumination aperture 220 may be moved along the probe 120 with the use of an actuator coupled to the light sleeve assembly 130. A position of the illumination aperture 220 relative to a distal end 123 of the probe 120 may be adjusted by manipulation of the actuator. FIGS. 5A and 5B illustrate an example vitrector 100 having an actuator 445 coupled to the light sleeve assembly 130 to adjust the position of the light sleeve assembly 130. The actuator 445 may be actuated by a finger of a user, such as a thumb. The actuator 445 may extend through a slot formed in a forward projecting portion 446 of the nose piece 115. The actuator 445 may be moved within a slot relative to the forward projection portion 446 and to extend or retract the light sleeve assembly 130 along the probe 120. The actuator 445 may be adhesively, mechanically, or otherwise coupled to the light sleeve assembly 130, or may engage the light sleeve assembly 130 in a frictional engagement. Accordingly, as the actuator 445 is moved in the direction of arrow 230 or the direction of arrow 232, the light sleeve assembly 130 is moved in kind. By manipulation of the actuator 445, the light sleeve assembly 130 is moved accordingly along the probe 120. As a result, a position of the illumination aperture 220 along the probe 120 is adjusted. Other types of actuators (for example, pneumatic, hydraulic, electrical, or other) may also be utilized. Further, the actuator of may be operable to adjust a position of the light sleeve assembly 130 without manual manipulation of the light sleeve assembly 130. Further, the actuator, whether manual or otherwise, may be utilized to adjust a position of the light sleeve assembly 130 relative to the probe 120 without removing the probe 120 from the eye.

Figure 6A:
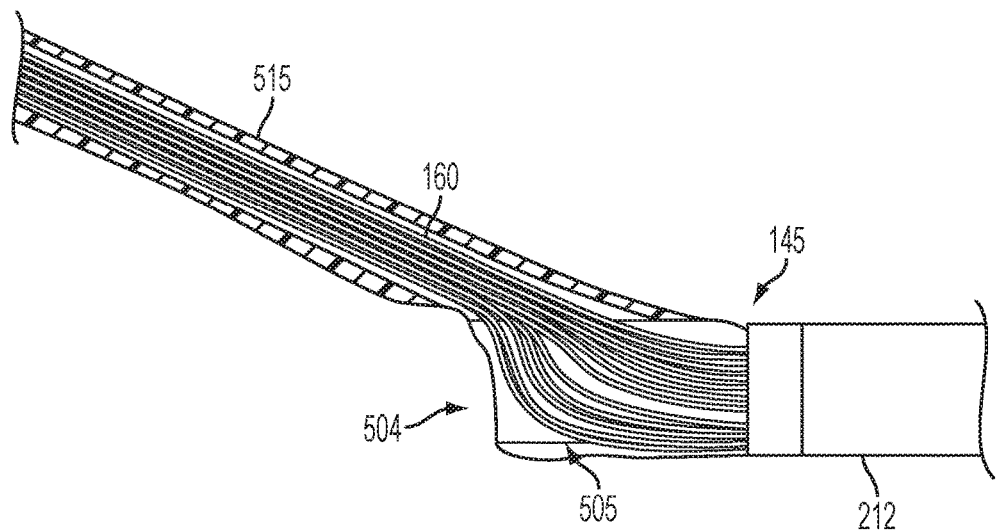
FIG. 6A is a detailed view of a proximal end of an example light sleeve assembly showing a transition area of a plurality of optical fibers.
Figure 6B:
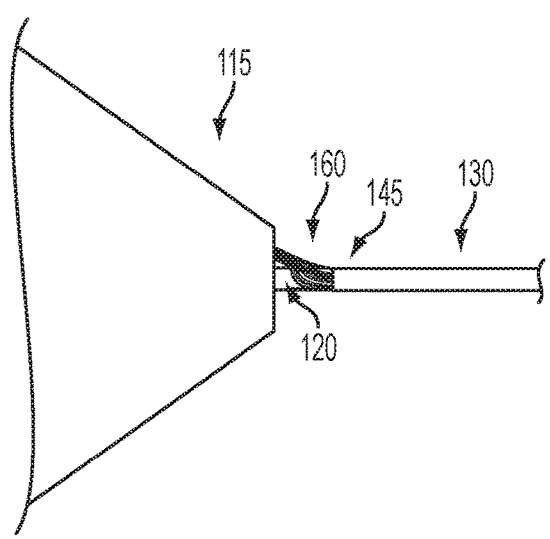
FIG. 6B is a detailed view of a proximal end of an example light sleeve assembly, illustrating the sheath and encapsulated array of optical fibers thereof.
Figure 6C:
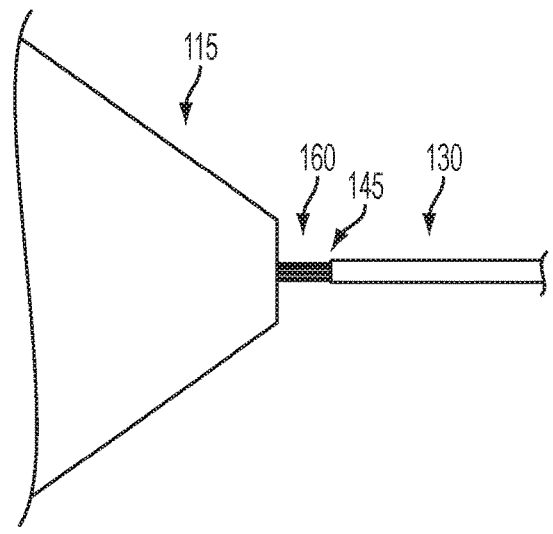
FIG. 6C is a top view of the vitrectomy instrument shown in FIG. 6B.

As shown in FIGS. 1B, 4A, 5A, 5B, the proximal end 145 of the light sleeve assembly 130 may be slidably received within the nose piece 115, with the light sleeve assembly 130 extending along the probe 120. Referring to FIGS. 6A, 6B, and 6C, the optical fibers 210 exit the proximal end 145 of the sleeve 212 of the light sleeve assembly 130 at a transition area 504. Within the transition zone 504, the optical fibers 210 may be encapsulated in an encapsulant 505. As shown in FIG. 6A, the optical fibers 210 are gather to a side of the probe 120, and the probe 120 extends proximally beyond the transition area 504 of the optical fibers 210. Beyond the transition area 504, the optical fibers 210 may be arranged into a fiber bundle 160. The fiber bundle 160 may be disposed within a protective sheath 515. The protective sheath 515 is operable to protect the optical fibers 210 and as well as provide strain relief to the optical fibers 210. In some instances, the protective sheath 515 may be formed from an elastomeric material. However, the protective sheath 515 may be formed from any suitable material. The encapsulant 505 may also encapsulate at least a portion of the optical fibers 210 that extend into and through the protective sheath 515.

Figure 6D:
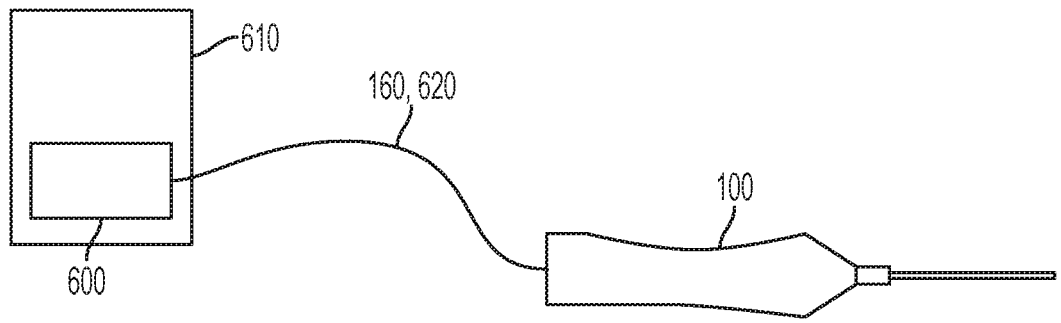
FIG. 6D is a schematic view of an example vitrector coupled to a surgical console.

In some implementations, the fiber bundle 160 may extend to and be coupled with a light source. In some implementations, as shown in FIG. 6D, light source 600 may be disposed remote from the vitrector 100. For example, the light source 600 may be provided in a surgical console 610 to which the vitrector 100 is coupled. In other implementations, the fiber bundle 160 may be coupled to one or more secondary optical fibers 620 which connect to or extend from the light source 600. In still other implementations, the light source may be contained within or otherwise coupled to the housing 110 of the vitrector 100. As explained above, the light source may reside at a surgical console 610, and light generated by the light source 600 may be provided to the vitrector 100 and delivered via the secondary optical fibers 620 and/or fiber bundle 160 to optical fibers 210 for illuminating the surgical site.

Figure 6E:
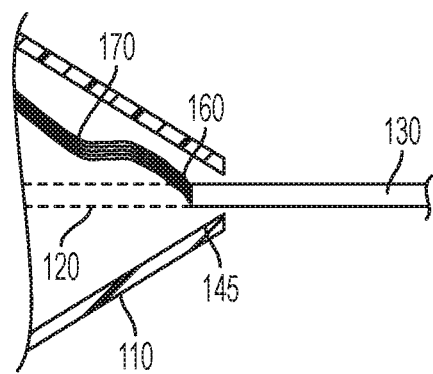
FIG. 6E is a detail view of a portion of an example vitrectomy instrument illustrating a proximal end of a light sleeve assembly retracted into a housing of the vitrectomy instrument showing the plurality of optical fibers in a slackened configuration.

In some implementations, the fiber bundle 160 may be extendable from and retractable into the housing 110 in response to movement of the light sleeve assembly 130 along the probe 120, as depicted in FIGS. 6B (extended configuration) and 6E (retracted configuration). Thus, in some instances, the housing 110 may include space to accommodate at least a portion of the fiber bundle 160. Also, the fiber bundle 160 may include slack 170, i.e., a length of the fiber bundle 160 inside the housing 110 so as to allow a desired amount of movement of the light sleeve assembly 130, as shown in FIG. 6E. Consequently, movement of the light sleeve assembly 130 relative to the probe 120 is made possible by having the light sleeve assembly 130 moveable within and relative to the nose piece 115 and providing a sufficient length of the fiber bundle 160 to allow sliding of the light sleeve assembly 130 along the probe 120 to the distal end thereof FIG. 6E depicts the proximal end 145 of the light sleeve assembly 130 in a first position in which the fiber bundle 160 is in a slackened configuration. In some implementations, when the light sleeve assembly 130 is moved to this first position, the distal end 146 of the light sleeve assembly 130 is spaced away from the distal end 123 of the probe 120. For example, FIG. 3B shows the light sleeve assembly 130 displaced proximally from the distal end 123 of the probe 120. The light sleeve assembly 130 is movable to a second position in which the light sleeve assembly 130 is in an extended configuration. In the extended configuration, the distal end 146 of the light sleeve assembly 130 is positioned closer to the distal end 123 of the probe 120. The fiber bundle 160 in this second position is in a less slackened condition. In some instances, the second position, the fiber bundle 160 may be substantially taut. In other instances, the fiber bundle 160 may have a lessened amount of slack than in the first position. FIG. 3C shows an example light sleeve assembly 130 disposed closer to the distal end 123 of the probe 120.

Figure 7A:
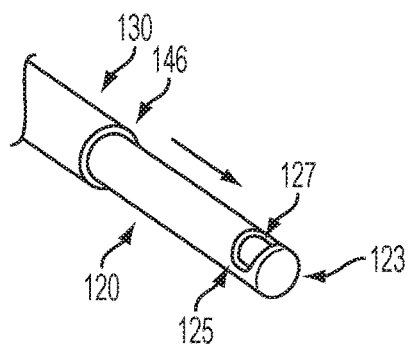
FIGS. 7A to 7B are perspective views illustrating an example vitrectomy cutter assembly with a diathermy function.
Figure 7B:
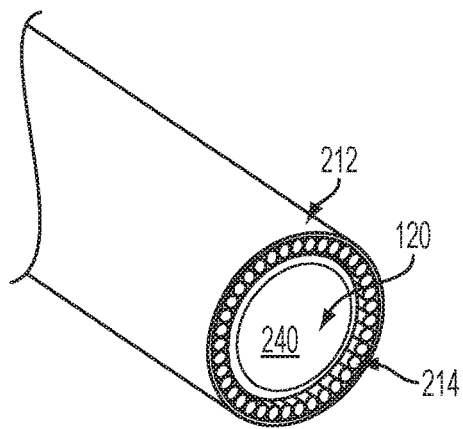

In still other implementations, the vitrector 100 may incorporate a wet field diathermy capability. In some instances, a vitrectomy procedure may result in bleeding of vessels about the retina. Diathermy is the application of electricity (typically high frequency alternating current) to induce heat. The induced heat may be utilized to cauterizing vessels to stop bleeding. The diathermy capability may be implemented with a metal used to form or included in the sleeve 212 and the metal forming probe 120. The close proximity between the sleeve 212 and the probe 120, particularly when the light sleeve assembly 130 is extended such that the end face 222 of the light sleeve assembly 130 is substantially flush with the end surface 240 of probe 120 (as shown, for example, in FIG. 7B), generates an electrical field as a result of application of the high frequency alternating current. An electric field effect is generated between the probe 120 the sleeve 212 with the encapsulant 214 acting as an insulator for diathermy operations. The generated electrical field induces heating of material, such as tissues and more particularly blood vessels, located adjacent to the distal end 123 of the probe 120. In the context of bleeding vessels, the generated heat cauterizes the vessels, thereby stopping the bleeding.

To provide a diathermy capability, metal incorporated into or forming the sleeve 212 may be connected to a first pole of a generator, with the probe 120 connected to a second pole of a generator. Again, the encapsulant 214 surrounding the optical fibers may be used as an insulating material. For example, the encapsulant 214 may be formed form a material having sufficient dielectric strength to serve as an insulator. An electric field is generated between the two poles such that the vitrector 100 is operable to provide a diathermy function. For example, as explained above, the diathermy capability may be operable when the light sleeve assembly 130 is positioned substantially flush with the end surface 240 of the probe 120. The generated electric field induces heat within tissues disposed adjacent the distal end 123 of the probe 120. The generated heat may be utilized to cauterization tissues. For example, blood vessels within the eye, particularly bleeding vessels about the retina, may be cauterized to stop bleeding. Inclusion of a diathermy capability with the vitrector 100 avoids the need to exchange the vitrector 100 with a diathermy probe when diathermy is needed. Eliminating this exchange reduces time required to perform a surgical procedure and eliminates potential injury to ocular tissues that may be associated with withdrawing and inserting instruments from and into the eye. Thus, when diathermy is needed, the light sleeve assembly 130 may be positioned as described. When diathermy is not desired, the light sleeve assembly 130 may be located at another position or positions to provide illumination as described above.

Figure 8A:
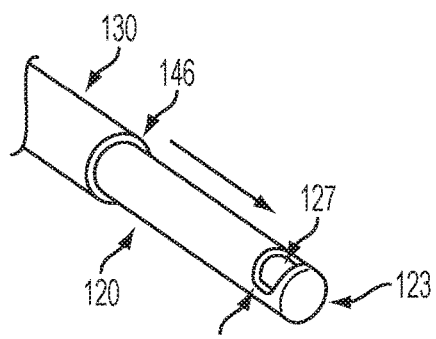
FIGS. 8A to 8B are perspective views illustrating an example vitrectomy cutter assembly with an endolaser function.
Figure 8B:
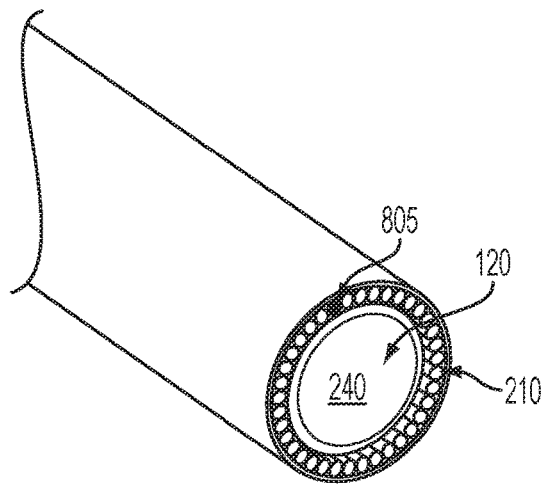

In some implementations, the vitrector 100 may incorporate an endolaser capability. An endolaser treatment involves the use of laser radiation, for example in the context of retinal surgical procedures, to seal tears in the retina. The vitrector 100 may incorporate endolaser functionality by replacing one or more of the optical fibers 210 used to provide illumination with one or more optical fibers having properties suitable for transmitting laser light. FIGS. 8A-8B show an example vitrector 100 operable to provide endolaser capability with an optical fiber 805 provided among the optical fibers 210. In operation, the distal end 146 of the light sleeve assembly 130 may to be positioned substantially flush with the end surface 240 of the probe 120. A flush arrangement of the light sleeve assembly 130 and the end surface 240 avoids laser vignetting by the probe 120. Also, the inclusion of an endolaser capability with the vitrector 100 eliminates the need to remove the vitrector 100 in order to insert a separate endolaser probe, thereby reducing risks associated with surgical procedures, such as one or the risks explained above.

At least one optical fiber 805 with properties appropriate for endolaser may be added to the array of optical fibers 210. While the remaining optical fibers 210 in the array continue to provide illumination, the optical fiber 805 may be coupled to a laser source. For example, the optical fiber 805 may have a distal end that is terminated with a connector appropriate for a laser source. The optical fiber 805 may extend along the length of the probe 120 in a manner similar to the remaining optical fibers 210. When endolaser functionality is required, the light sleeve assembly 130 may be moved to a position flush with the end surface 240 and the optical fiber 805 activated for the transmission of laser light from the distal end of the optical fiber 805. Consequently, at times, the vitrector 100 may be utilized to provide illumination, for example, as described above, while, at other times, the vitrector 100 may be utilized to provide endolaser functionality.

In still other implementations, the vitrector 100 may incorporate a wet field diathermy capability and an endolaser capability, while also including an illumination capability. A user, such as a surgeon, may select a type of vitrector 100, such as a vitrector having an illumination capability, a vitrector with illumination and one or more of an endolaser or diathermy capability, based on the therapy(ies) that is/are believed to be needed during a surgical procedure.

In some instances, application of illumination, diathermy, or endolaser functionality may be implemented by actuation of a corresponding control on a surgical console to which the vitrector is coupled. For example, where a diathermy capability may be desired, a user may position the light sleeve assembly 130 such that the distal end 146 thereof is substantially flush with the end face 240 of the probe 120. The user may then actuate a diathermy control of the surgical console to provide the diathermy function of the vitrector 100. When the endolaser control of the surgical console is actuated, the endolaser function is provided by the vitrector 100. As explained above, in some instances, a user may align the distal end 146 of the light sleeve assembly 130 with the end face 240 of the probe 120 in order to eliminate vignetting of the emitted laser light.

The foregoing description generally illustrates and describes various implementations of the present disclosure. It will, however, be understood by those skilled in the art that various changes and modifications can be made to one or more of the features described herein without departing from the spirit and scope of the disclosure, and that it is intended that all matter contained in the above description or shown in the accompanying drawings shall be interpreted as being illustrative, and not to be taken in a limiting sense. Furthermore the scope of the present disclosure shall be construed to cover various modifications, combinations, additions, alterations, etc., above and to the above-described embodiments, which shall be considered to be within the scope of the present disclosure. Accordingly, various features and characteristics of the present disclosure as discussed herein may be selectively interchanged and applied to other illustrated and non-illustrated examples of the present disclosure, and numerous variations, modifications, and additions further can be made thereto without departing from the spirit and scope of the present disclosure as set forth in the appended claims.

What is claimed is:

1. An illuminated vitrectomy instrument comprising:
   a vitrectomy probe; and
   a light sleeve assembly extending along and substantially surrounding the vitrectomy probe and having a position adjustable along a length of the vitrectomy probe, the light sleeve assembly comprising:
   a plurality of optical fibers, at least a first portion of the optical fibers operable to provide illumination, each of the optical fibers comprising an end face;
   an illumination aperture circumjacent at least a portion of the vitrectomy probe, the illumination aperture defined by the end faces of the optical fibers and operable to provide an area of illumination, the area of illumination variable in response to the position of the light sleeve assembly relative to the vitrectomy probe;
   a sleeve, wherein the plurality of optical fibers is arranged in an array along an inner surface of the sleeve; and
   an encapsulant encapsulating the plurality of optical fibers;
   wherein the sleeve is configured to be connected to a first pole of a generator,
   wherein the vitrectomy probe is configured to be connected to a second pole of the generator,
   wherein the encapsulant defines an insulating layer disposed between the sleeve and the vitrectomy probe, and
   wherein an alternating current applied to the sleeve and the vitrectomy probe is operable to generate an electric field therebetween to produce a diathermy function when the distal end of the light sleeve assembly is positioned substantially flush with the end. surface of the vitrectomv probe.

2. The illuminated vitrectomy instrument of claim 1, further comprising:
   a nose piece at least partially housing the vitrectomy probe,
   wherein a proximal end of the light sleeve assembly is received within the nose piece and a distal end of the light sleeve assembly terminates proximally to a distal end of the vitrectomy probe, and
   wherein a distance between the distal end of the light sleeve assembly and the distal end of the vitrectomy probe is altered in response to a change in the position of the light sleeve assembly relative to the vitrectomy probe.

3. The illuminated vitrectomy instrument of claim 1, wherein the position of the light sleeve assembly is manually adjusta.ble.

4. The illuminated vitrectomy instrument of claim 1, further comprising an actuator coupled to the light sleeve assembly, wherein the position of the light sleeve assembly with respect to the vitrectomy probe is adjusted by manipulation of the actuator.

5. The illuminated vitrectomy instrument of claim 1, wherein at least one of plurality of optical fibers comprises a fiber operable to propagate laser light.

6. The illuminated vitrectomy instrument of claim 1, wherein the light sleeve assembly further comprising a transition area where the plurality of optical fibers are gathered to a side of the vitrectomy probe in a fiber bundle.

7. The illuminated vitrectomy instrument of claim 6, wherein the fiber bundle is disposed within a protective sheath to provide strain relief to the plurality of optical fibers.

8. The illumination vitrectomy instrument of claim 1, wherein, during use, a position of the light sleeve assembly is adjustable to any position between a region defined by a distal end of the light sleeve assembly and a distal end of the vitrectomy probe.

9. The illumination vitrectomy probe of claim 1, wherein the vitrectomy probe comprises an outer cutter and a port formed in the outer cutter.

10. The illuminated vitrectomy instrument of claim 1, wherein at least a second portion of the optical fibers are operable to provide laser light for endolaser functionality.

11. An illuminated vitrectomy cutter assembly, comprising
   a housing;
   a vitrectomy probe having a proximal end received within the housing and a freely extending distal end; and
   a light sleeve assembly movable along the vitrectomy probe between the proximal end and the distal end of the vitrectomy probe, the light sleeve assembly comprising:
   a first end adjacent the housing;
   a second end opposite the first end;
   a plurality of optical fibers arranged in an array about the vitrectomy probe, at least a first portion of the plurality of optical fibers operable to provide illumination, each of the optical fibers comprising an end face;
   an illumination aperture formed at the second end of the light sleeve assembly, the illumination aperture defined by the end faces of the optical fibers, the illumination aperture operable to provide collective illumination comprising the individual illumination from each of the plurality of optical fibers;
   a sleeve, wherein the plurality of optical fibers is arranged in an array along an inner surface of the sleeve; and
   an encapsulant substantially encapsulating the plurality of optical fibers along at least a portion of the sleeve;
   wherein the sleeve is configured to be connected to a first pole of a generator;
   wherein the vitrectomy probe is configured to be connected to a second pole of a generator;
   wherein the encapsulant defines an insulating layer disposed between the sleeve and the vitrectomy probe; and wherein, upon application of an alternating current to the sleeve and the vitrectomy probe, an electric field is generated between the sleeve and the vitrectomy probe to produce a diathermy function when the second end of the light sleeve assembly is positioned substantially flush with an end surface of the vitrectomy probe.

12. The illuminated vitrectomy cutter assembly of claim 11, wherein the light sleeve assembly further comprises a transition area where the plurality of optical fibers are gathered to a side of the vitrectomy probe in a fiber bundle.

13. The illuminated vitrectomy cutter assembly of claim 12, wherein the fiber bundle is disposed within a protective sheath to provide strain relief to the plurality of optical fibers.

14. The illuminated vitrectomy cutter assembly of claim 11, wherein the collective illumination of the plurality of optical fibers defines an area of illumination, and wherein the area of illumination is adjusted in response to movement of the light sleeve assembly along the vitrectomy probe.

15. The illuminated vitrectomy cutter assembly of claim 11, further comprising a nose piece coupled to the housing, the nose piece configured to receive a proximal end of the light sleeve assembly.

16. The illuminated vitrectomy cutter assembly of claim 11, wherein at least one of the plurality of optical fibers comprises a fiber operable to propagate laser light.

17. The illumination vitrectomy cutter assembly of claim 11, wherein, during use, a position of the light sleeve assembly is adjustable to any position between a region defined by a distal end of the light assembly and a distal end of the vitrectom probe.

18. The illumination vitrectomy cutter assembly of claim 11, wherein the vitrectomy probe comprises an outer cutter and a port formed in the outer cutter.

19. The illuminated vitrectomy cutter assembly of claim 11, wherein at least a second portion of the optical fibers are operable to provide laser light for endolaser functionality.

* * * * *